(12) United States Patent
Tsukamoto et al.

(10) Patent No.: US 10,364,218 B2
(45) Date of Patent: Jul. 30, 2019

(54) METHOD OF PRODUCING EPSILON-CAPROLACTAM

(71) Applicant: Toray Industries, Inc., Tokyo (JP)

(72) Inventors: Daijiro Tsukamoto, Kamakura (JP);
Masateru Ito, Kamakura (JP);
Katsushige Yamada, Kamakura (JP);
Kohei Yamashita, Nagoya (JP);
Masato Akahira, Nagoya (JP); Koji Yamauchi, Nagoya (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 15/758,664

(22) PCT Filed: Sep. 8, 2016

(86) PCT No.: PCT/JP2016/076389
§ 371 (c)(1),
(2) Date: Mar. 8, 2018

(87) PCT Pub. No.: WO2017/043560
PCT Pub. Date: Mar. 16, 2017

(65) Prior Publication Data
US 2018/0237389 A1 Aug. 23, 2018

(30) Foreign Application Priority Data
Sep. 11, 2015 (JP) .................................. 2015-179243

(51) Int. Cl.
| | | |
|---|---|---|
| *C07D 201/08* | (2006.01) | |
| *B01J 23/44* | (2006.01) | |
| *C07D 223/10* | (2006.01) | |
| *C07C 59/245* | (2006.01) | |
| *B01J 21/04* | (2006.01) | |
| *B01J 21/06* | (2006.01) | |
| *B01J 21/08* | (2006.01) | |
| *B01J 21/18* | (2006.01) | |
| *B01J 23/20* | (2006.01) | |
| *B01J 23/26* | (2006.01) | |
| *B01J 23/42* | (2006.01) | |
| *B01J 23/46* | (2006.01) | |
| *B01J 23/72* | (2006.01) | |
| *C07B 61/00* | (2006.01) | |

(52) U.S. Cl.
CPC ............ *C07D 201/08* (2013.01); *B01J 21/04* (2013.01); *B01J 21/063* (2013.01); *B01J 21/066* (2013.01); *B01J 21/08* (2013.01); *B01J 21/18* (2013.01); *B01J 23/20* (2013.01); *B01J 23/26* (2013.01); *B01J 23/42* (2013.01); *B01J 23/44* (2013.01); *B01J 23/464* (2013.01); *B01J 23/466* (2013.01); *B01J 23/468* (2013.01); *B01J 23/72* (2013.01); *C07C 59/245* (2013.01); *C07D 223/10* (2013.01); *C07B 61/00* (2013.01); *Y02P 20/52* (2015.11)

(58) Field of Classification Search
CPC .................................................. C07D 201/08
See application file for complete search history.

(56) References Cited

U.S. PATENT DOCUMENTS

| 8,946,411 B2 | 2/2015 | Dias et al. |
|---|---|---|
| 2007/0244317 A1 | 10/2007 | Crabtree et al. |
| 2009/0305364 A1 | 12/2009 | Burgard et al. |
| 2013/0030215 A1 | 1/2013 | Bui et al. |
| 2017/0320819 A1 | 11/2017 | Ito et al. |

FOREIGN PATENT DOCUMENTS

| JP | 2007-509914 | 4/2007 |
|---|---|---|
| JP | 2011-515111 A | 5/2011 |
| JP | 2012-59 A | 1/2012 |
| JP | 2015-517977 A | 6/2015 |
| WO | 2012/141997 A1 | 10/2012 |
| WO | 2013/126250 A1 | 8/2013 |
| WO | 2014/043182 A2 | 3/2014 |
| WO | 2016/068108 A1 | 5/2016 |

OTHER PUBLICATIONS

Yu, J.-L. et al., "Direct biosynthesis of adipic acid from a synthetic pathway in recombinant *Escherichia coli*", *Biotechnology and Bioengineering*, 2014, vol. 111, Issue 12, pp. 2580-2586, Abstract only.

Bugg, T. D. H. et al., "Pathways for degradation of lignin in bacteria and fungi", *Natural Product Reports*, 2011, vol. 28, Issue 12, pp. 1883-1896.

Draths, K. M. et al., "Environmentally compatible synthesis of catechol from D-glucose", *Journal of the American Chemical Society*, 1995, vol. 117, Issue 9, pp. 2395-2400.

*Primary Examiner* — Emily A Bernhardt
*Assistant Examiner* — Laura M Daniel
(74) *Attorney, Agent, or Firm* — DLA Piper LLP (US)

(57) ABSTRACT

A method of producing ε-caprolactam from 3-oxoadipic acid includes: step 1 of mixing at least one selected from the group consisting of 3-oxoadipic acid and salts thereof with a catalyst and a solvent in the presence of hydrogen to produce 3-hydroxyadipic acid; and step 2 of reacting the 3-hydroxyadipic acid which is a product of step 1, a salt or carboxylic acid derivative thereof, or a mixture of these with hydrogen and ammonia.

21 Claims, No Drawings

METHOD OF PRODUCING EPSILON-CAPROLACTAM

TECHNICAL FIELD

This disclosure relates to a method of producing ε-caprolactam which can be used as a material for polyamides.

BACKGROUND

ε-Caprolactam is an important chemical material that can be used as a material for polyamides and the like, and is industrially produced worldwide. It is mostly used as a material for Nylon 6 which is a polyamide.

As an industrial production method of ε-caprolactam, a production method using the Beckmann rearrangement reaction with fuming sulfuric acid from cyclohexanone oxime has been widely employed. That production method uses crude oil as the original material. From the viewpoint of possible depletion of fossil resources in the future, and the problem of global warming due to emission of greenhouse gases by mining and use of fossil resources, development of a method of producing ε-caprolactam using an alternative material is necessary. In particular, development of methods of producing ε-caprolactam from biomass, which is a renewable resource, or from a substance derivable from biomass resources, has been demanded.

WO 2013/126250 discloses a method of producing ε-caprolactam by reacting adipic acid with hydrogen and ammonia in the presence of a heterogeneous catalyst and tert-butanol. As disclosed in JP 2011-515111 A and Biotechnology and Engineering, vol. 111, pp. 2580-2586(2011), adipic acid is a substance that is derivable from biomass resources because it can be produced from sugar by fermentation.

WO 2012/141997 also discloses a method of producing ε-caprolactam by reacting muconic acid with hydrogen and ammonia in the presence of a catalyst. As disclosed in US 2013/0030215 A1, muconic acid is a substance that is derivable from biomass resources and can be produced from glucose by fermentation.

3-Oxoadipic acid is a $C_6$ dicarboxylic acid having a carbonyl group. JP 2012-59 A discloses a method in which 3-oxoadipic acid is produced from protocatechuic acid or vanillic acid by fermentation. Natural Product Reports, vol. 28, pp. 1883-1896(2011) discloses that protocatechuic acid and vanillic acid can be obtained by the decomposition of lignin which is a major component of plants. Journal of the American Chemical Society, vol. 117, pp. 2395-2400(1995) discloses a method in which protocatechuic acid is produced from glucose by fermentation. It can thus be said that 3-oxoadipic acid is derivable from lignin or sugar.

WO 2014/043182 discloses a method of producing 3-hydroxyadipic acid by reacting 3-oxoadipic acid with hydrogen in the presence of a catalyst and a solvent.

By the method disclosed in WO 2013/126250, ε-caprolactam can be produced from adipic acid. However, adipic acid is considered to have a low efficiency in the derivation thereof from biomass resources and is not preferred as a biomass-resource material for ε-caprolactam. For example, JP 2011-515111 A discloses a method of producing adipic acid from glucose by fermentation, but does not describe any actual working example of producing adipic acid, and it is unclear whether or not the method can actually produce adipic acid. In general, when a substance is produced using a microorganism, it is desirable that oxidation-reduction balance determined by the ratio of NADH to $NAD^+$ in cells be maintained, but that suggests that the oxidation-reduction balance is not maintained, and thus it is thought that such a method is difficult to produce adipic acid. According to the method disclosed in Biotechnology and Engineering, vol. 111, pp. 2580-2586(2011), the yield of adipic acid on the basis of glucose is 0.008 mol %, which is low.

By the method disclosed in WO 2012/141997, ε-caprolactam can be produced from muconic acid. However, muconic acid has a low efficiency in the derivation thereof from biomass resources and is not preferred as a material for ε-caprolactam. According to the method disclosed in US 2013/0030215 A1, the yield of muconic acid on the basis of glucose is 30 mol %, which is low and not a sufficiently satisfactory value.

In contrast, 3-oxoadipic acid can be derived from biomass resources at a high efficiency. According to the method disclosed in JP 2012-59 A, the yield of 3-oxoadipic acid is 100 mol % on the basis of protocatechuic acid or vanillic acid which is a lignin decomposition product. According to the method disclosed in Journal of the American Chemical Society, vol. 117, pp. 2395-2400(1995), the yield of protocatechuic acid on the basis of glucose is 50 mol %. From the aforementioned descriptions, it is considered that 3-oxoadipic acid is a substance derivable from a lignin decomposition product or glucose at a high efficiency, and is preferred as a material for ε-caprolactam which is derivable from biomass resources.

However, there has been no report hitherto on a method of converting 3-oxoadipic acid into ε-caprolactam. 3-Oxoadipic acid is a compound whose basic structure is a $C_6$ dicarboxylic acid similar to adipic acid and muconic acid. However, as shown in Comparative Example 1 herein, the direct application of the method described in WO 2012/141997 to 3-oxoadipic acid was found not to produce ε-caprolactam at all. In other words, it turned out that a method of converting muconic acid to ε-caprolactam cannot be applied directly to 3-oxoadipic acid.

It could therefore be helpful to provide a method of producing ε-caprolactam from 3-oxoadipic acid which is preferred as a biomass resource.

SUMMARY

We found that, as shown by Scheme 1, ε-caprolactam can be produced by sequentially carrying out the steps of mixing 3-oxoadipic acid with a catalyst and a solvent in the presence of hydrogen (step 1); and the step of reacting the product of step 1 with hydrogen and ammonia (step 2).

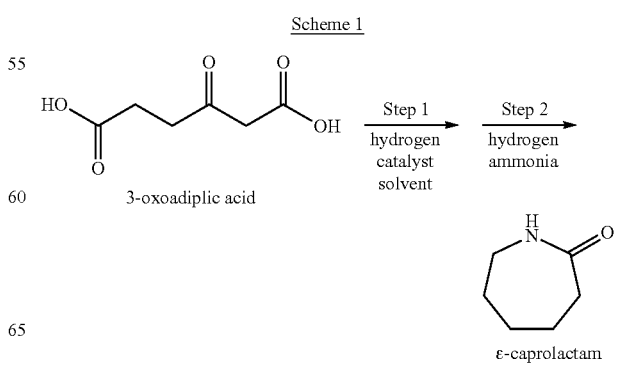

We thus provide (1) to (11):

(1) A method of producing ε-caprolactam, comprising step 1 of mixing at least one selected from the group consisting of 3-oxoadipic acid and salts thereof with a catalyst and a solvent in the presence of hydrogen to produce 3-hydroxyadipic acid; and step 2 of reacting the 3-hydroxyadipic acid which is a product of step 1, a salt or carboxylic acid derivative thereof, or a mixture of these with hydrogen and ammonia.

(2) The method according to (1), wherein the solvent is an aqueous solvent or an organic solvent having a polarity value of 0 to 0.3.

(3) The method according to (1) or (2), wherein the solvent is an organic solvent that mainly contains at least one selected from the group consisting of ether solvents and ester solvents.

(4) The method according to any one of (1) to (3), wherein the solvent is an organic solvent that mainly contains at least one selected from tetrahydrofuran, dioxane, 1,2-dimethoxyethane, diglyme, and ethyl acetate.

(5) The method according to any one of (1) to (4), wherein step 1 is carried out under the condition of the following (i) or (ii):
(i) in an aqueous solvent at a reaction temperature of 0° C. to 50° C.;
(ii) in an organic solvent having a polarity value of 0 to 0.3 at a reaction temperature of not lower than 0° C. and lower than 75° C.

(6) The method according to any one of (1) to (5), wherein step 2 is carried out in the presence of a catalyst.

(7) The method according to any one of (1) to (6), wherein the catalyst used in step 1 and/or step 2 includes one or more metals selected from the group consisting of palladium, platinum, ruthenium, rhodium, rhenium, nickel, iridium, osmium, copper, and chromium.

(8) The method according to (7), wherein the metal is supported on at least one support selected from the group consisting of alumina, carbon, silica, titania, zirconia, tantalum oxide, niobium oxide, and zeolite.

(9) The method according to any one of (1) to (8), wherein the partial pressure of hydrogen in step 1 and step 2 is 0.1 MPa to 10 MPa at ordinary temperature in terms of the gauge pressure.

(10) The method according to any one of (1) to (9), wherein the reaction temperature in step 2 is 150° C. to 280° C.

(11) A method of producing 3-hydroxyadipic acid, comprising mixing at least one selected from the group consisting of 3-oxoadipic acid and salts thereof with a catalyst in the presence of hydrogen under the condition of the following (i) or (ii):
(i) in an aqueous solvent at a reaction temperature of 0° C. to 50° C.;
(ii) in an organic solvent having a polarity value of 0 to 0.3 at a reaction temperature of not lower than 0° C. and lower than 75° C.

We thus make it possible to produce ε-caprolactam from 3-oxoadipic acid which can be derived from biomass resources at a high efficiency. Because 3-oxoadipic acid can be derived from a variety of biomass resources (such as lignin and sugar), our methods are useful for the stable production of ε-caprolactam from biomass resources.

We also make it possible to produce 3-hydroxyadipic acid from 3-oxoadipic acid in a short step while suppressing by-production of levulinic acid.

DETAILED DESCRIPTION

Our methods will be described below in more detail.

The phase "biomass resources" means regenerative organic resources derived from organisms, which are resources composed of organic matters that plants produce by carbon dioxide fixation using solar energy. Specific examples of the biomass resources include maize, sugarcane, tubers, wheat, rice, soybean, pulp, kenaf, rice straw, wheat straw, bagasse, corn, stover, switchgrass, weeds, waste paper, woods, charcoal, natural rubber, cotton, soybean oil, palm oil, safflower oil, and castor oil.

The phase "substances derivable from biomass resources" means substances that are derived, that can be derived, or that were derived, from biomass resources by fermentation, chemical conversion or the like.

The 3-oxoadipic acid used herein is a substance derivable from biomass resources, as described above. Specifically, as shown by Scheme 2, a method in which 3-oxoadipic acid is produced by fermentation from protocatechuic acid or vanillic acid each derived from lignin or glucose, can be illustrated. For example, as described in Natural Product Reports, vol. 28, pp. 1883-1896(2011), protocatechuic acid or vanillic acid can be produced by decomposing lignin using *Pseudomonas paucimobilis*, *Sphingomonas paucimobilis*, or the like. As described in Journal of the American Chemical Society, vol. 117, pp. 2395-2400(1995), protocatechuic acid can be produced at a yield of 50 mol % by fermentation from glucose using *Escherichia coli* into which the *Klebsiella pnuemoniae* aroZ gene is incorporated. From protacatechuic acid or vanillic acid which is thus obtained, 3-oxoadipic acid can be produced at a yield of 100 mol % by fermentation, using genetically engineered *Pseudomonas putida*, as described in JP 2012-59 A.

Scheme 2

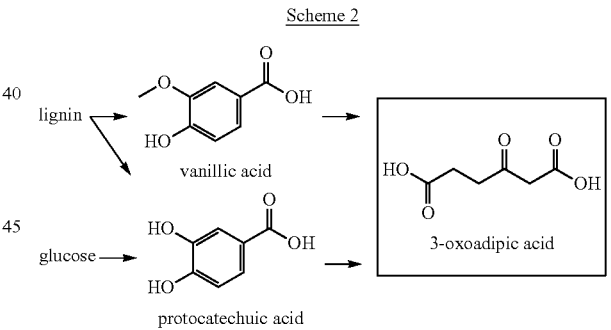

Our methods enable 3-oxoadipic acid derivable from biomass resources to be used as a material, but fossil resources such as petroleum can also be used as a material.

The 3-oxoadipic acid may be any of free compound, a salt, and a mixture of free compound and a salt. The salt to be used may be a monovalent salt or a divalent salt. Examples of monovalent salts include 3-oxoadipic acid monoammonium salt, 3-oxoadipic acid monolithium salt, 3-oxoadipic acid monosodium salt, and 3-oxoadipic acid monopotassium salt. Examples of divalent salts include 3-oxoadipic acid diammonium salt, 3-oxoadipic acid dilithium salt, 3-oxoadipic acid disodium salt, 3-oxoadipic acid dipotassium salt, 3-oxoadipic acid magnesium salt, and 3-oxoadipic acid calcium salt. A mixture of different salts among these may also be used.

The method of producing ε-caprolactam comprises step 1 of mixing 3-oxoadipic acid with a catalyst and a solvent in the presence of hydrogen; and step 2 of reacting the product of step 1 with hydrogen and ammonia.

Examples of the solvents used in step 1 include, but are not limited to, organic solvents such as alcoholic solvents such as methanol, ethanol, propanol, and butanol; halogen-containing solvents such as carbon tetrachloride, dichloromethane, and chloroform; aliphatic hydrocarbon solvents such as pentane, hexane, heptane, octane, and decane; aromatic hydrocarbon solvents such as benzene, toluene, and xylene; ether solvents such as dimethylether, diethylether, 1,2-dimethoxyethane, diglyme, tetrahydrofuran, and dioxane; ester solvents such as methyl acetate, ethyl acetate, n-propyl acetate, n-butyl acetate; organic solvents such as γ-butyrolactone; N-methylpyrrolidone; and dimethylsulfoxide; and aqueous solvents such as water and solvent mixtures in which water as a main component (i.e., more than 50 vol %, preferably 90 vol % or more) is mixed at an optional ratio with an organic solvent soluble in water. A mixed solvent of two or more kinds of these may also be used.

Step 1 reacts 3-oxoadipic acid with hydrogen in the presence of a catalyst, and hence it is preferable to use a solvent which can dissolve 3-oxoadipic acid and is not hydrogenated under the reaction conditions of step 1, from the viewpoint of shortening of reaction time and suppression of byproducts. As such a solvent, an aqueous solvent or an organic solvent having a polarity value of 0 to 0.3 can preferably be used.

As used herein, a polarity value, which is generally known as an $E_T^N$ value, is a polarity parameter of a solvent determined using the phenomenon in which the maximum wavelength in the absorption spectrum of a pyridinium-N-phenoxide betaine derivative remarkably varies with the polarity of the solvent, and water (1.000) and tetramethylsilane (0.000) are used as reference solvents (Handbook of Chemistry: Pure Chemistry I, 5th Ed., 770 (2004), compiled by The Chemical Society of Japan, Maruzen Publishing Co., Ltd.). For polarity values of various solvents, for example, "Chemical Reviews, vol. 94, No. 8, 2319-2358 (1994)" can be referred to, and the polarity value of a solvent whose polarity value is unknown and of a solvent mixture can be measured by the method described in the literature.

Examples of organic solvents having a polarity value of 0 to 0.3 include n-pentane (0.006), n-hexane (0.009), n-heptane (0.012), n-octane (0.012), n-nonane (0.009), n-decane (0.009), n-dodecane (0.012), cyclohexane (0.006), chloroform (0.259), bromoform (0.216), benzene (0.111), toluene (0.099), p-xylene (0.074), 3-ethyl-3-pentanol (0.241), 2,4-dimethyl-3-pentanol (0.290), 3-ethyl-2,4-dimethyl-3-pentanol (0.222), dimethyl ether (<0.2), diethyl ether (0.117), ethylvinyl ether (0.170), di-n-propyl ether (0.102), di-n-butyl ether (0.071), tert-butyl methyl ether (0.124), dimethoxymethane (0.157), diethoxymethane (0.099), 1,2-dimethoxyethane (0.231), diglyme (0.244), diethylene glycol diethyl ether (0.210), triglyme (0.253), furan (0.164), tetrahydrofuran (0.207), thiophene (0.145), tetrahydrothiophene (0.185), tetrahydropyran (0.170), 1,4-dioxane (0.164), anisole (0.198), dibenzyl ether (0.173), diphenyl ether (0.142), 3-pentanone (0.265), 2-hexanone (0.290), isobutylmethyl ketone (0.269), tert-butylmethyl ketone (0.256), diisopropyl ketone (0.247), di-n-butyl ketone (0.210), cyclopentanone (0.269), cyclohexanone (0.281), methyl acetate (0.253), acetate ethyl (0.228), vinyl acetate (0.225), n-propyl acetate (0.210), n-butyl acetate (0.241), methyl acrylate (0.250), methyl methacrylate (0.222), dimethyl carbonate (0.232), diethyl carbonate (0.185), tert-butylamine (0.179), diethylamine (0.145), triethylamine (0.043), trisn-butylamine (0.043), pyrrolidine (0.259), piperidine (0.148), carbon disulfide (0.065), and the like. The values in parentheses indicate polarity values.

Among organic solvents having a polarity value of 0 to 0.3, solvents that mainly contain an ether solvent such as dimethyl ether, diethyl ether, 1,2-dimethoxyethane, diglyme, tetrahydrofuran, or dioxane, or mainly contain an ester solvent such as methyl acetate, ethyl acetate, n-propyl acetate, or n-butyl acetate can preferably be used, and particularly solvents that mainly contain tetrahydrofuran, dioxane, 1,2-dimethoxyethane, diglyme, or ethyl acetate can more preferably be used. The phrase "mainly contain" refers to containing a substance at a concentration of more than 50 vol %, preferably a concentration of 90 vol % or more, further preferably a concentration of 100 vol %.

The organic solvents having a polarity value of 0 to 0.3 used in Examples herein and their respective polarity values are methanol (0.762), isopropanol (0.546), and tert-butanol (0.389). The values in parentheses indicate polarity values.

The reaction temperature in step 1 is preferably 0° C. to 100° C. but is not limited thereto. When an aqueous solvent is used, the reaction temperature is preferably 0° C. to 50° C., and when an organic solvent having a polarity value of 0 to 0.3 is used, the reaction temperature is preferably not lower than 0° C. and lower than 75° C. For either solvent, the reaction temperature is more preferably 10° C. to 40° C. When the reaction temperature is high, 3-oxoadipic acid tends to be thermally decomposed, and on the other hand, when the reaction temperature is too low, the reaction rate tends to be decreased. It is convenient to carry out the reaction at ordinary temperature at which no device for heating or cooling is required.

As the metal contained in the catalyst used in step 1, a transition metal is preferable, and specifically, the catalyst preferably contains one or more selected from the group consisting of palladium, platinum, ruthenium, rhodium, rhenium, nickel, iridium, osmium, copper, and chromium.

The metal contained in the catalyst used in step 1 may be supported on a support from the viewpoint of saving the amount of the metal used and increasing catalytic activity. Examples of the support include carbon and metal oxides such as alumina, silica, titania, zirconia, tantalum oxide, niobium oxide, zeolite, tungsten oxide, and magnesia; and composite oxides of these metal oxides such as silica alumina, silica titania, silica magnesia, and alumina zirconia. The ratio of the metal weight to the total weight of the support and the metal supported on the support is usually 0.1 to 10% by weight.

When the aforementioned supported metal catalyst is used, the catalyst is preferably used after being activated by heat treatment under an atmosphere of hydrogen or an inert gas such as nitrogen, helium, or argon before reaction.

When the aforementioned supported metal catalyst is used, the catalyst can be easily recovered by solid-liquid separation after completion of reaction. The recovered catalyst may be used repeatedly, in which case it is preferable to reactivate the catalyst by heat treatment under an atmosphere of hydrogen or an inert gas such as nitrogen, helium, or argon.

The partial pressure of hydrogen in step 1 is not limited to a particular value but is preferably 0.1 MPa to 10 MPa (gauge pressure), more preferably 0.5 MPa to 3 MPa (gauge pressure), at ordinary temperature, because the partial pressure of hydrogen that is too low prolongs reaction time and because the partial pressure of hydrogen that is too high is undesirable in view of facilities safety. The gas to be used may be a gas mixture of hydrogen and an inert gas such as nitrogen, helium, or argon.

The content of at least one selected from the group consisting of 3-oxoadipic acid and salts thereof in the reaction mixture at the start of step 1 is not limited to a particular value but is usually about 0.1 to 50 parts by weight, preferably about 1 to 10 parts by weight, relative to 100 parts by weight of the solvent.

The reaction of step 1 can be carried out with either a batch or continuous method.

3-Hydroxyadipic acid is a reaction intermediate in the method of producing ε-caprolactam including step 1 and step 2. That is, as shown by Scheme 3, a product containing 3-hydroxyadipic acid is obtained from 3-oxoadipic acid in step 1, and ε-caprolactam is produced from the 3-hydroxyadipic acid in step 2.

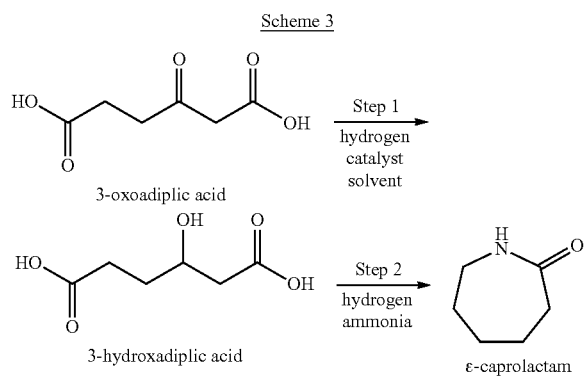

It is important to carry out step 1 and step 2 separately and sequentially such that 3-hydroxyadipic acid is once obtained as a product of step 1. When the method described in WO 2012/141997 is applied to 3-oxoadipic acid here, the 3-oxoadipic acid is exposed to a condition under which hydrogen and ammonia coexist from the beginning of the reaction. However, in this case, it is difficult to obtain ε-caprolactam of interest, as shown in Comparative Examples 1 and 2 described below. This is believed to be because 3-oxoadipic acid is unstable to heat or ammonia. The method is different from the method described in WO 2012/141997 in that ammonia is not present in first step 1. Thus, step 1 is preferably carried out in the substantial absence of ammonia. The phrase "in the substantial absence of" refers to a condition wherein the ammonia concentration is 100 ppm or less, preferably 10 ppm or less, most preferably 0 ppm.

Carrying out step 1 yields an unpurified product containing not only 3-hydroxyadipic acid but also byproducts, the solvent, the catalyst and the like. This unpurified product may be subjected to step 2 without carrying out separation, purification or the like. Alternatively, a roughly purified product containing 3-hydroxyadipic acid may be obtained by removing the catalyst and/or the solvent roughly from the mixture and then used in step 2. Still alternatively, 3-hydroxyadipic acid may be isolated and purified from the aforementioned roughly purified product and then used in step 2.

The catalyst can be removed by an ordinary unit operation such as extraction, adsorption, filtration, precipitation, and centrifugation. Because a heterogeneous catalyst can be removed from the reaction solution by an easy solid-liquid separation operation such as filtration, precipitation, and centrifugation, it is preferable from the viewpoint of easy separation that a heterogeneous catalyst be used when 3-hydroxyadipic acid is isolated and purified after step 1.

The solvent can be removed by an ordinary unit operation such as evaporation, drying, distillation, and extraction. The removed solvent can be recycled for use in step 1.

As a method of isolating and purifying 3-hydroxyadipic acid from the roughly purified product, an ordinary method such as extraction, membrane separation, column chromatography, ion exchange resin treatment, crystallization, and recrystallization can be used.

In step 2, the 3-hydroxyadipic acid obtained in step 1 can be used in the form of free compound or a salt, or can be used after being converted to a carboxylic acid derivative (acid anhydride, ester, amide), or a mixture of these can be used. Examples of salts and carboxylic acid derivatives of 3-hydroxyadipic acid include 3-hydroxyadipic acid monoammonium salt, 3-hydroxyadipic acid monolithium salt, 3-hydroxyadipic acid monosodium salt, 3-hydroxyadipic acid monopotassium salt, 3-hydroxyadipic acid diammonium salt, 3-hydroxyadipic acid dilithium salt, 3-hydroxyadipic acid disodium salt, 3-hydroxyadipic acid dipotassium salt, 3-hydroxyadipic acid magnesium salt, 3-hydroxyadipic acid calcium salt, 3-hydroxyadipic acid anhydride, 3-hydroxyadipic acid monomethyl ester, 3-hydroxyadipic acid dimethyl ester, 3-hydroxyadipic acid monoethyl ester, 3-hydroxyadipic acid diethyl ester, 3-hydroxyadipic acid monoamide, 3-hydroxyadipic acid diamide and the like.

Our methods make it possible to produce 3-hydroxyadipic acid from 3-oxoadipic acid in step 1 that is a single step. The catalyst and the solvent used in producing 3-hydroxyadipic acid from 3-oxoadipic acid are those described above used in step 1, and the solvent to be used is preferably the aforementioned aqueous solvent or organic solvent having a polarity value of 0 to 0.3 from the viewpoint of shortening the reaction time and suppression of byproducts. When the solvent used is an aqueous solvent, the reaction temperature is preferably 0° C. to 50° C., and when the solvent used is an organic solvent having a polarity value of 0 to 0.3, the reaction temperature is preferably not lower than 0° C. and lower than 75° C.

Next, step 2 will be described. In step 2, the 3-hydroxyadipic acid which is a product of step 1, a salt or carboxylic acid derivative thereof, or at least one selected from the group consisting of 3-hydroxyadipic acid and a salt and a carboxylic acid derivative thereof is reacted with hydrogen and ammonia.

In step 2, the reaction can be enhanced by performing the reaction in the presence of a catalyst. Either a homogeneous catalyst or a heterogeneous catalyst can be used as the catalyst.

As the metal contained in the catalyst, a transition metal is preferable, and specifically, the catalyst preferably contains one or more selected from the group consisting of palladium, platinum, ruthenium, rhodium, rhenium, nickel, iridium, osmium, copper, and chromium.

The metal contained in the catalyst used in step 2 may be supported on a support from the viewpoint of saving the amount of the metal used and increasing the catalytic activity. Examples of the support include carbon and metal oxides such as alumina, silica, titania, zirconia, tantalum oxide, niobium oxide, zeolite, tungsten oxide, and magnesia; and composite oxides of these metal oxides (for example, silica alumina, silica titania, silica magnesia, and alumina zirconia). The ratio of the metal weight to the total weight of the support and the metal supported on the support is usually 0.1 to 10% by weight.

When the aforementioned supported metal catalyst is used, the catalyst is preferably used after being activated by heat treatment under an atmosphere of hydrogen or an inert gas such as nitrogen, helium, or argon before reaction.

When the aforementioned supported metal catalyst is used, the catalyst can be easily recovered by solid-liquid separation after completion of reaction. The recovered catalyst may be used repeatedly, in which case it is preferable to reactivate the catalyst by heat treatment under an atmosphere of hydrogen or an inert gas such as nitrogen, helium, or argon.

The partial pressure of hydrogen in step 2 is not limited to a particular value but is preferably 0.1 MPa to 10 MPa (gauge pressure) at ordinary temperature, more preferably 0.5 MPa to 3 MPa (gauge pressure) at ordinary temperature, because the partial pressure of hydrogen that is too low prolongs reaction time and because the partial pressure of hydrogen that is too high is undesirable in view of facilities safety. The gas to be used may be a gas mixture of hydrogen and an inert gas such as nitrogen, helium, or argon.

The ammonia to be used may be added to a reactor in either a gaseous state or a liquid state. When the ammonia is added to a reactor in a liquid state, liquid ammonia or a solution in which ammonia is dissolved may be used. For example, an aqueous ammonia solution, ammonia solution in dioxane, ammonia solution in chloroform, ammonia solution in ether, ammonia solution in alcohol, or the like may be used. When gaseous ammonia is used, the partial pressure thereof is not limited to a particular value, but it is preferably 0.1 MPa to 5 MPa (gauge pressure) at ordinary temperature, more preferably 0.1 MPa to 1 MPa (gauge pressure) at ordinary temperature, because the reaction time is prolonged when the partial pressure is too low.

Hydrogen and ammonia may be independently added to a reactor, and may be added as a hydrogen-ammonia gas mixture which is previously prepared. The order of adding hydrogen and ammonia is not limited to a particular one.

The reaction temperature in step 2 is preferably 100° C. to 350° C., more preferably 150° C. to 280° C., but is not limited thereto. When the reaction temperature is too low, the reaction tends not to progress sufficiently, and when the reaction temperature is too high, by-production of compounds other than ε-caprolactam which is a substance of interest is promoted, making it unlikely to afford a satisfactory yield.

Examples of the solvent used in step 2 include, but are not limited to, alcoholic solvents such as methanol, ethanol, propanol, and butanol; halogen-containing solvents such as carbon tetrachloride, dichloromethane, and chloroform; aliphatic hydrocarbon solvents such as pentane, hexane, heptane, octane, and decane; aromatic hydrocarbon solvents such as benzene, toluene, and xylene; ether solvents such as dimethylether, diethylether, 1,2-dimethoxyethane, diglyme, tetrahydrofuran, and dioxane; ester solvents such as methyl acetate, ethyl acetate, n-propyl acetate, n-butyl acetate; γ-butyrolactone; N-methylpyrrolidone; dimethylsulfoxide; and water. A solvent mixture of two or more kinds of these may also be used. An aprotic solvent such as dioxane, diglyme, or tetrahydrofuran is preferably used.

The content of 3-hydroxyadipic acid, a salt or carboxylic acid derivative thereof, or a mixture thereof in the reaction mixture at the start of step 2 is not limited to a particular value but is usually about 0.1 to 10 parts by weight, preferably about 1 to 5 parts by weight, relative to 100 parts by weight of the solvent.

The reaction of step 2 can be carried out with either a batch or continuous method.

Steps 1 and 2 can be carried out sequentially in the same reactor (one-pot). Carrying out the reaction in the same reactor is preferable for the sake of facilities.

When steps 1 and 2 are carried out sequentially in the same reactor, step 2 can be carried out directly after step 1 without removal of the catalyst used in step 1 from the reactor. Further, another catalyst may be added to the catalyst used in step 1, or the catalyst used in step 1 may be removed and replaced by another catalyst. Among these, the procedure in which the catalyst used in step 1 is not removed and used also in step 2 is convenient and economical.

When steps 1 and 2 are carried out sequentially in the same reactor, step 2 can be carried out after step 1 without removal of the solvent used in step 1. Further, another solvent may be added to the solvent used in step 1, or the solvent used in step 1 may be removed and replaced by another solvent. Among these, the procedure in which the solvent used in step 1 is not removed and used also in step 2 is convenient and economical.

When steps 1 and 2 are carried out sequentially in the same reactor, step 2 can be carried out adding ammonia to the reactor without discharging the hydrogen remaining in the reactor at the completion of step 1 to the outside of the reactor. Alternatively, step 2 may be carried out with hydrogen and ammonia freshly added to the reactor after the hydrogen remaining in the reactor at the completion of step 1 is discharged out of the reactor, or step 2 may be carried out after replacing the remaining hydrogen by an inert gas such as nitrogen, helium, or argon and then freshly adding hydrogen and ammonia.

In the method of producing ε-caprolactam, ε-caprolactam can be recovered by an ordinary separation purification operation(s) such as filtration, extraction, and/or distillation after completion of step 2. The hydrogen and the ammonia may be recycled into the reaction system.

The ε-caprolactam obtained by the method of producing ε-caprolactam can be used as a material for production of polyamides. As a method of producing the polyamide, a known method in which ε-caprolactam is subjected to ring-opening polymerization may be applied (see Osamu Fukumoto eds., "Polyamide Resin Handbook", Nikkan Kogyo Shimbun, Ltd. (January, 1998)).

EXAMPLES

Our methods will be described below in detail by way of Examples. However, this disclosure is not limited to the Examples below.

In Examples 1 to 8 and Comparative Examples 1 and 2, the product yields which were reaction results were determined by equation (1). The term "feed" refers to 3-oxoadipic acid.

$$\text{Product yield (mol \%)} = \text{product yield (mol)}/\text{amount of initial feed (mol)} \times 100 \quad (1)$$

In Examples 9 to 24, the material conversion ratios and product selectivity which were reaction results were determined by equations (2) and (3), respectively. The term "feed" refers to 3-oxoadipic acid.

$$\text{Feed conversion (mol \%)} = \text{feed consumption (mol)}/\text{amount of initial feed (mol)} \times 100 \quad (2)$$

$$\text{Product selectivity (mol \%)} = \text{product yield (mol)}/\text{feed consumption (mol)} \times 100 \quad (3)$$

The reaction solution was analyzed by gas chromatography (GC) and high-performance liquid chromatography (HPLC). The product was quantitated with an absolute calibration curve prepared using an authentic sample. The quantitative analysis of ε-caprolactam was carried out by GC, and the quantitative analyses of 3-oxoadipic acid, 3-hydroxyadipic acid, and levulinic acid were carried out by HPLC. The analysis conditions of GC and HPLC are shown below.

GC Analysis Conditions:
GC device: GC2010 plus (manufactured by Shimadzu Corporation)
Column: InertCap for amines; 30 m in length; 0.32 mm in inner diameter (manufactured by GL Sciences Inc.)
Carrier gas: helium; constant linear velocity (40.0 cm/second)
Vaporizing chamber temperature: 250° C.
Detector temperature: 250° C.
Column oven temperature: 100° C.→(10° C./minute)→230° C. for 3 minutes (16 minutes in total)
Detector: FID
HPLC Analysis Conditions:
HPLC device: Prominence (manufactured by Shimadzu Corporation)
Column: Synergi hydro-RP (manufactured by Phenomenex Inc.); 250 mm in length; 4.60 mm in inner diameter; 4 μm in particle size
Mobile phase: 0.1% by weight aqueous phosphoric acid solution/acetonitrile=95/5 (volume ratio)
Flow rate: 1.0 mL/minute
Detector: UV (210 nm)
Column temperature: 40° C.

Reference Example 1

Provision of 3-Oxoadipic Acid

The 3-oxoadipic acid used in our method was provided by chemical synthesis.

First, 1.5 L of super-dehydrated tetrahydrofuran (manufactured by Wako Pure Chemical Industries, Ltd.) was added to 13.2 g (0.1 mol) of succinic acid monomethyl ester (manufactured by Wako Pure Chemical Industries, Ltd.), and 16.2 g (0.1 mol) of carbonyldiimidazole (manufactured by Wako Pure Chemical Industries, Ltd.) was added thereto with stirring, followed by stirring the resulting mixture under nitrogen atmosphere at room temperature for 1 hour. To this suspension, 15.6 g (0.1 mol) of malonic acid monomethyl ester potassium salt and 9.5 g (0.1 mol) of magnesium chloride were added. The resulting mixture was stirred under nitrogen atmosphere at room temperature for 1 hour, and then stirred at 40° C. for 12 hours. After completion of the reaction, 0.05 L of 1 mol/L hydrochloric acid was added to the mixture at room temperature, and extraction with ethyl acetate was carried out. By separation and purification by silica gel column chromatography (hexane:ethyl acetate=1:5), 13.1 g of pure 3-oxohexanedicarboxylic acid dimethyl ester was obtained. Yield: 70%.

To 5 g (0.026 mol) of the obtained 3-oxohexanedicarboxylic acid dimethyl ester, 26 mL of methanol (manufactured by Kokusan Chemical Co., Ltd.) was added, and 12 mL of 5 mol/L aqueous sodium hydroxide solution was added to the resulting mixture with stirring, followed by stirring the mixture at room temperature overnight. After completion of the reaction, 12 mL of 5 mol/L hydrochloric acid was added to the mixture, and the resulting mixture was extracted with 100 mL of ethyl acetate (manufactured by Wako Pure Chemical Industries, Ltd.). The mixture was concentrated using a rotary evaporator and recrystallized with acetone/petroleum ether to afford 2 g of pure 3-oxoadipic acid. Yield: 47%.

Example 1

Production of ε-caprolactam by sequentially carrying out two steps of: mixing 3-oxoadipic acid with a catalyst and a solvent in the presence of hydrogen (step 1); and reacting the product of step 1 with hydrogen and ammonia (step 2)

Step 1

To a stainless steel autoclave having an internal capacity of 0.1 L (manufactured by Taiatsu Techno Corporation), 0.15 g of the 3-oxoadipic acid synthesized in Reference Example 1, 50 mL of dioxane (manufactured by Wako Pure Chemical Industries, Ltd.), 0.05 g of palladium (5% on gamma alumina powder, reduced (manufactured by Alfa Aesar)) and 0.2 g of 5% Pt alumina powder (manufactured by N. E. Chemcat Corporation) were added. After the inside of the autoclave was purged with nitrogen, hydrogen gas was introduced into the autoclave such that the internal pressure of the autoclave became 0.9 MPa (gauge pressure), and then the resulting mixture was stirred at 500 rpm at room temperature for 24 hours. The gas in the autoclave was released to allow the pressure to decrease to ordinary pressure. A part of the reaction solution was sampled and analyzed by HPLC. The results are shown in Table 1.

Step 2

After step 1, ammonia gas was introduced into the autoclave such that the internal pressure of the autoclave became 0.18 MPa (gauge pressure), followed by stirring the mixture at 500 rpm at room temperature for 45 minutes. While the stirring was continued, hydrogen was introduced into the autoclave such that the internal pressure of the autoclave was adjusted to 0.72 MPa (gauge pressure) in terms of the hydrogen partial pressure (total pressure (gauge pressure): 0.9 MPa). Subsequently, the temperature in the autoclave was increased to 250° C. in 15 minutes. After being retained at 250° C. for 7 hours, the autoclave was left to stand to room temperature, and the gas in the autoclave was released to allow the pressure to decrease to ordinary pressure. The reaction solution was then recovered. After 50 mL of water was added and mixed into the solution, the catalyst was removed by centrifugation, and the supernatant was analyzed by GC and HPLC. The results are shown in Table 1.

Comparative Example 1

Reaction of 3-Oxoadipic Acid with Hydrogen and Ammonia by the Method Disclosed in WO 2012/141997

To a stainless steel autoclave having an internal capacity of 0.1 L (manufactured by Taiatsu Techno Corporation), 0.15 g of the 3-oxoadipic acid synthesized in Reference Example 1, 50 mL of dioxane (manufactured by Wako Pure Chemical Industries, Ltd.), and 0.05 g of palladium (5% on gamma alumina powder, reduced (manufactured by Alfa Aesar)) were added. After the inside of the autoclave was purged with nitrogen, ammonia gas was introduced into the autoclave such that the internal pressure of the autoclave was adjusted to 0.18 MPa (gauge pressure), and then the resulting mixture was stirred at 500 rpm at room temperature for 45 minutes. While the stirring was continued, hydrogen was introduced into the autoclave such that the internal pressure of the autoclave was adjusted to 0.72 MPa (gauge pressure) in terms of the hydrogen partial pressure (total pressure (gauge pressure): 0.90 MPa). Subsequently, the temperature in the autoclave was increased to 250° C. in 1 hour. After being retained at 250° C. for 3 hours, the autoclave was left to stand to room temperature, and the gas in the autoclave was released to allow the pressure to decrease to ordinary pressure. The reaction solution was then recovered. After 50 mL of water was added and mixed into the solution, the catalyst was removed by centrifugation, and the supernatant was analyzed by GC and HPLC. The results are shown in Table 1.

Comparative Example 2

Reaction of 3-Oxoadipic Acid with Hydrogen and Ammonia Using the Same Material, Solvent, and Catalyst as in Example 1 by the Same Reaction Operation as in Comparative Example 1

To a stainless steel autoclave having an internal capacity of 0.1 L (manufactured by Taiatsu Techno Corporation), 0.15 g of the 3-oxoadipic acid synthesized in Reference Example 1, 50 mL of dioxane (manufactured by Wako Pure Chemical Industries, Ltd.), 0.05 g of 5% Pd alumina powder (palladium (5% on gamma alumina powder, reduced (manufactured by Alfa Aesar))) and 0.2 g of 5% Pt alumina powder (manufactured by N. E. Chemcat Corporation) were added. After the inside of the autoclave was purged with nitrogen, ammonia gas was introduced into the autoclave such that the internal pressure of the autoclave was adjusted to 0.18 MPa (gauge pressure), and then the resulting mixture was stirred at 500 rpm at room temperature for 45 minutes. While the stirring was continued, hydrogen was introduced into the autoclave such that the internal pressure of the autoclave was adjusted to 0.72 MPa (gauge pressure) in terms of the hydrogen partial pressure (total pressure (gauge pressure): 0.9 MPa). Subsequently, the temperature in the autoclave was increased to 250° C. in 15 minutes. After being retained at 250° C. for 6 hours, the autoclave was left to stand to room temperature, and the gas in the autoclave was released to allow the pressure to decrease to ordinary pressure. The reaction solution was then recovered. After 50 mL of water was added and mixed into the solution, the catalyst was removed by centrifugation, and the supernatant was analyzed by GC and HPLC. The results are shown in Table 1.

Reference Example 2

Preparation of Catalyst

To an aqueous solution of palladium nitrate ($Pd(NO_3)_2 \cdot 2H_2O$) (0.13 g) dissolved in 10 mL of water, 1 g of niobium oxide ($Nb_2O_5$, manufactured by Wako Pure Chemical Industries, Ltd.) was added, and the resulting mixture was stirred at room temperature for 3 hours. From the mixture, water was evaporated using an evaporator at 20 mmHg at 40° C., and the resulting powder was dried at 110° C. overnight and calcined under a stream of air at 500° C. for 4 hours. Subsequently, the powder was treated under a stream of hydrogen at 400° C. for 2 hours to thereby afford 5% Pd supported on niobium oxide ($Pd/Nb_2O_5$). The phrase "5%" means that the ratio of Pd to the sum of the weights of Pd and a support is 5% by weight at the time of feeding the materials. In a similar manner, 5% Pd supported on tantalum oxide ($Pd/Ta_2O_5$) and 5% Pd supported on zirconia ($Pd/ZrO_2$) were prepared using tantalum oxide ($Ta_2O_5$, manufactured by Wako Pure Chemical Industries, Ltd.) and zirconia ($ZrO_2$, reference catalyst No. JRC-ZRO-3 of Catalysis Society of Japan) as supports, respectively.

Example 2

The reaction was carried out in the same manner as in Example 1 except that: 0.1 g of 5% Pd supported on niobium oxide prepared in Reference Example 2 and 0.03 g of 5% Pt supported on carbon (Platinum on carbon, 5 wt. % loading, matrix activated carbon support; manufactured by Sigma-Aldrich) were used as catalysts; in step 1, the reaction temperature was 30° C., and the reaction time was 14.5 hours; and the autoclave was retained at 250° C. for 6 hours in step 2. The results are shown in Table 1.

Example 3

The reaction was carried out in the same manner as in Example 2 except that: 0.1 g of 5% Pd supported on tantalum oxide prepared in Reference Example 2 and 0.025 g of 5% Pt supported on carbon were used as catalysts; the reaction time in step 1 was 19 hours; and the autoclave was retained at 250° C. for 4 hours in step 2. The results are shown in Table 1.

Example 4

The reaction was carried out in the same manner as in Example 2 except that: in place of 5% Pd supported on niobium oxide, 0.1 g of 5% Pd supported on zirconia prepared in Reference Example 2 was used; as a solvent, 1,2-dimethoxyethane (manufactured by Wako Pure Chemical Industries, Ltd.) was used in place of dioxane; the reaction time in step 1 was 18 hours; and the autoclave was retained at 250° C. for 5 hours in step 2. The results are shown in Table 1.

Example 5

The reaction was carried out in the same manner as in Example 2 except that: 0.1 g of Palladium (5% on gamma alumina powder, reduced (manufactured by Alfa Aesar)) and 0.05 g of 5% Pt supported on carbon were used as catalysts; the reaction time in step 1 was 14.5 hours; and in step 2, the temperature in the autoclave was increased to 180° C. in 15 minutes, retained for 1 hour, increased to 250° C. in 8 minutes, and retained at 250° C. for 4.7 hours. The results are shown in Table 1.

Example 6

The reaction was carried out in the same manner as in Example 2 except that: 0.2 g of 5% Pd supported on niobium oxide and 0.05 g of 5% Pt supported on carbon were used as catalysts; the reaction time in step 1 was 16 hours; and in step 2, the temperature in the autoclave was increased to 180° C. in 15 minutes, retained for 2 hours, increased to 250° C. in 8 minutes, and retained at 250° C. for 8 hours. The results are shown in Table 1.

Example 7

The reaction was carried out in the same manner as in Example 6 except that, in step 2, the temperature in the autoclave was increased to 150° C. in 10 minutes, retained for 1 hour, increased to 200° C. in 8 minutes, retained for 1 hour, increased to 250° C. in 8 minutes, and retained at 250° C. for 20 hours. The results are shown in Table 1.

Example 8

The reaction was carried out in the same manner as in Example 1 except that: a stainless steel autoclave having an internal capacity of 0.2 L (manufactured by Taiatsu Techno Corporation), 0.3 g of 3-oxoadipic acid, 100 mL of dioxane (manufactured by Kanto Chemical Co., Inc.), 0.1 g of palladium (5% on gamma alumina powder, reduced (manufactured by Alfa Aesar)) and 5% Pt supported on carbon (manufactured by N. E. Chemcat Corporation) 0.2 g were used; in step 1, the mixture was stirred under an internal hydrogen gas pressure of 1.45 MPa (gauge pressure) at 30° C. at 1000 rpm for 7 hours; and, in step 2, the internal pressure of ammonia gas was 0.05 MPa (gauge pressure), the stirring rate was 1000 rpm, the partial pressure of hydrogen was 1.45 MPa (gauge pressure) (total pressure (gauge pressure): 1.5 MPa), and the temperature in the autoclave was increased to 250° C. in 1 hour and retained at 250° C. for 3 hours. The results are shown in Table 1.

Example 9

Production of 3-Hydroxyadipic Acid by Mixing 3-Oxoadipic Acid with a Catalyst and a Solvent in the Presence of Hydrogen To a stainless steel autoclave having an internal capacity of 30 mL (manufactured by Taiatsu Techno Corporation), 16 mg of 3-oxoadipic acid synthesized in Reference Example 1, 10 mL of water, and 10 mg of 5% Pt supported on carbon (Platinum on carbon, 5 wt. % loading, matrix activated carbon support; manufactured by Sigma-Aldrich) were added. After the inside of the autoclave was purged with nitrogen, hydrogen gas was introduced into the autoclave such that the internal pressure of the autoclave became 0.9 MPa (gauge pressure), and then the reaction was carried out by stirring the resulting mixture at 500 rpm at room temperature for 1 hour. The gas in the autoclave was released to allow the pressure to decrease to ordinary pressure. The reaction solution was analyzed by HPLC. The results are shown in Table 2.

Example 10

The reaction was carried out in the same manner as in Example 9 except that the reaction temperature was 40° C. The results are shown in Table 2.

Example 11

The reaction was carried out in the same manner as in Example 9 except that the reaction temperature was 60° C. The results are shown in Table 2.

Example 12

The reaction was carried out in the same manner as in Example 9 except that the reaction temperature was 80° C. The results are shown in Table 2.

Example 13

The reaction was carried out in the same manner as in Example 9 except that the catalyst used was 5% Pt supported on alumina (manufactured by N. E. Chemcat Corporation) and that the reaction time was 24 hours. The results are shown in Table 2.

Example 14

The reaction was carried out in the same manner as in Example 9 except that the solvent used was dioxane (manufactured by Wako Pure Chemical Industries, Ltd.). The results are shown in Table 2.

Example 15

The reaction was carried out in the same manner as in Example 14 except that the reaction temperature was 40° C. The results are shown in Table 2.

Example 16

The reaction was carried out in the same manner as in Example 14 except that the reaction temperature was 60° C. The results are shown in Table 2.

Example 17

The reaction was carried out in the same manner as in Example 14 except that the reaction temperature was 80° C. The results are shown in Table 2.

Example 18

The reaction was carried out in the same manner as in Example 14 except that the reaction temperature was 120° C. The results are shown in Table 2.

Example 19

The reaction was carried out in the same manner as in Example 9 except that the solvent used was tetrahydrofuran (manufactured by Wako Pure Chemical Industries, Ltd.). The results are shown in Table 2.

Example 20

The reaction was carried out in the same manner as in Example 9 except that the solvent used was ethyl acetate (manufactured by Wako Pure Chemical Industries, Ltd.). The results are shown in Table 2.

Example 21

The reaction was carried out in the same manner as in Example 9 except that the solvent used was methanol (manufactured by Kokusan Chemical Co., Ltd.). The results are shown in Table 2.

Example 22

The reaction was carried out in the same manner as in Example 9 except that the solvent used was isopropanol (manufactured by Wako Pure Chemical Industries, Ltd.). The results are shown in Table 2.

Example 23

The reaction was carried out in the same manner as in Example 9 except that the solvent used was tert-butyl alcohol (manufactured by Wako Pure Chemical Industries, Ltd.). The results are shown in Table 2.

Example 24

The reaction was carried out in the same manner as in Example 14 except that the catalyst used was 5% Rh supported on carbon (Rhodium on carbon, 5 wt. % loading; manufactured by Sigma-Aldrich). The results are shown in Table 2.

TABLE 1

Production of ε-caprolactam from 3-oxoadipic acid

| | Catalyst | Solvent | Step 1 | Step 2 | Results of Step 1 3-hydroxyadipic acid Yield (mol %) | Results of Step 2 3-hydroxyadipic acid Yield (mol %) | ε-caprolactam Yield (mol %) |
|---|---|---|---|---|---|---|---|
| Example 1 | Pd/Al$_2$O$_3$ Pt/Al$_2$O3 | dioxane | H$_2$ 0.9 MPa RT, 23 h | H$_2$ 0.72 MPa NH$_3$ 0.18 MPa 250° C., 7 h | 61 | not detected | 27 |
| Example 2 | Pd/Nb$_2$O$_5$ Pt/C | dioxane | H$_2$ 0.9 MPa 30° C., 14.5 h | H$_2$ 0.72 MPa NH$_3$ 0.18 MPa 250° C., 7 h | 94 | not detected | 21 |
| Example 3 | Pd/ZrO$_2$ Pt/C | dioxane | H$_2$ 0.9 MPa 30° C. 19 h | H$_2$ 0.72 MPa NH$_3$ 0.18 MPa 250° C., 6 h | 88 | not detected | 12 |
| Example 4 | Pd/ZrO$_2$ Pt/C | 1,2-dimethoxyethane | H$_2$ 0.9 MPa 30° C., 18 h | H$_2$ 0.72 MPa NH$_3$ 0.18 MPa 250° C., h | 45 | not detected | 17 |
| Example 5 | Pd/Al$_2$O$_3$ Pt/C | dioxane | H$_2$ 0.9 MPa 30° C., 14.5 h | H$_2$ 0.72 MPa NH$_3$ 0.18 MPa 180° C., 1 h 250° C., 4.7 h | 83 | not detected | 43 |
| Example 6 | Pd/Nb$_2$O$_5$ Pt/C | dioxane | H$_2$ 0.9 MPa 30° C., 16 h | H$_2$ 0.72 MPa NH$_3$ 0.18 MPa 180° C., 2h 250° C., 8 h | 89 | not detected | 46 |
| Example 7 | Pd/Nb$_2$O$_5$ Pt/C | dioxane | H$_2$ 0.9 MPa 30° C., 16 h | H$_2$ 0.72 MPa NH$_3$ 0.18 MPa 150° C., 1 h 200° C., 1 h 250° C., 20 h | 88 | not detected | 60 |
| Example 8 | Pd/Nb$_2$O$_5$ Pt/C | dioxane | H$_2$ 1.45 MPa 30° C., 7 h | H$_2$ 1.45 MPa NH$_3$ 0.05 MPa 250° C., 3 h | 86 | not detected | 29 |

| | Catalyst | Step | Results 3-hydroxyadipic acid Yield (mol %) | ε-caprolactam Yield (mol %) |
|---|---|---|---|---|
| Comparative Example 1 | Pd/Al$_2$O$_3$ | H$_2$ 0.72 MPa NH$_3$ 0.18 MPa 250° C., | not detected | not detected |
| Comparative Example 2 | Pd/Al$_2$O$_3$ Pt/Al$_2$O$_3$ | H$_2$ 0.72 MPa NH$_3$ 0.18 MPa 250° C., | not detected | not detected |

Pd/Al$_2$O$_3$: Palladium, 5% on gamma alumina powder, reduced
Pt/Al$_2$O$_3$: 5% Pt on alumina powder
Pt/C: Platinum on carbon, 5 wt. % loading, matrix activated carbon support
Pd/Nb$_2$O$_5$: 5% Pd supported on niobium oxide (Reference Example 2) Pd/Ta$_2$O$_5$: 5% Pd supported on tantalum oxide (Reference Example 2)
Pd/ZrO$_2$: 5% Pd supported on zirconia (Reference Example 2)

TABLE 2

Production of 3-hydroxadipic acid from 3-oxoadipic acid

| | Catalyst | Solvent | Reaction Temperature (° C.) | Feed Conversion (mol %) | 3-hydroxadipic acid Selectivity (mol %) | Levulinic Acid Selectivity (mol %) |
|---|---|---|---|---|---|---|
| Example 9 | Pt/C | water | room temperature | 74 | 97 | not detected |
| Example 10 | Pt/C | water | 40 | 95 | 96 | not detected |
| Example 11 | Pt/C | water | 60 | 100 | 77 | 10 |
| Example 12 | Pt/C | water | 80 | 100 | 25 | 50 |
| Example 13 | Pt/Al$_2$O$_3$ | dioxane | room temperature | 100 | 71 | not detected |
| Example 14 | Pt/C | dioxane | room temperature | 69 | 91 | not detected |
| Example 15 | Pt/C | dioxane | 40 | 87 | 93 | not detected |
| Example 16 | Pt/C | dioxane | 60 | 99 | 94 | not detected |
| Example 17 | Pt/C | dioxane | 80 | 100 | 97 | 2 |
| Example 18 | Pt/C | dioxane | 120 | 100 | 70 | 23 |
| Example 19 | Pt/C | tetrahydro-furan | room temperature | 21 | 93 | not detected |

TABLE 2-continued

Production of 3-hydroxadipic acid from 3-oxoadipic acid

|  | Catalyst | Solvent | Reaction Temperature (° C.) | Feed Conversion (mol %) | 3-hydroxadipic acid Selectivity (mol %) | Levulinic Acid Selectivity (mol %) |
| --- | --- | --- | --- | --- | --- | --- |
| Example 20 | Pt/C | ethyl acetate | room temperature | 73 | 100 | not detected |
| Example 21 | Pt/C | methanol | room temperature | 15 | 17 | 75 |
| Example 22 | Pt/C | isopropanol | room temperature | 83 | 76 | 24 |
| Example 23 | Pt/C | tert-butyl alcohol | room temperature | 55 | 72 | 24 |
| Example 24 | Rh/C | dioxane | room temperature | 52 | 94 | not detected |

In Examples 1 to 8, ε-caprolactam was obtained from 3-oxoadipic acid by carrying out the step of mixing 3-oxoadipic acid with a catalyst and a solvent in the presence of hydrogen (step 1); and the step of reacting the product of step 1 with hydrogen and ammonia (step 2). Further, the fact that 3-hydroxyadipic acid was obtained from 3-oxoadipic acid in step 1 and that the 3-hydroxyadipic acid was consumed to afford ε-caprolactam in step 2 has revealed that 3-hydroxyadipic acid is an intermediate in our production method.

On the other hand, in Comparative Example 1, 3-oxoadipic acid was allowed to react with hydrogen under the condition that ammonia coexisted from the beginning, as in the method described in WO 2012/141997, but ε-caprolactam was not produced.

In Comparative Example 2, the same catalysts and solvent as in Example 1 were used, but ε-caprolactam was not produced when 3-oxoadipic acid was allowed to react with hydrogen under the condition that ammonia coexisted from the beginning, as in the method described in WO 2012/141997.

These results revealed that it is important that, when 3-oxoadipic acid is used as a material, step 1 be carried out under the condition that ammonia does not coexist to afford 3-hydroxyadipic acid as an intermediate, and step 2 be then carried out under the condition that ammonia coexists.

Examples 9 to 24 revealed that 3-hydroxyadipic acid can be produced by mixing 3-oxoadipic acid with a catalyst and a solvent in the presence of hydrogen.

Examples 9 to 12 revealed that, by mixing 3-oxoadipic acid with a catalyst in an aqueous solvent in the presence of hydrogen at a reaction temperature of 0° C. to 50° C., 3-hydroxyadipic acid can be produced while the by-production of levulinic acid is suppressed.

Examples 13 to 16, 19 and 20 have revealed that, by mixing 3-oxoadipic acid with a catalyst in an organic solvent having a polarity value of 0 to 0.3 in the presence of hydrogen at a reaction temperature of not lower than 0° C. and lower than 75° C., 3-hydroxyadipic acid can be produced while by-production of levulinic acid is suppressed.

The invention claimed is:

1. A method of producing ε-caprolactam, comprising: step 1 of mixing at least one selected from the group consisting of 3-oxoadipic acid and salts thereof with a catalyst and a solvent in the presence of hydrogen to produce 3-hydroxyadipic acid; and step 2 of reacting the 3-hydroxyadipic acid which is a product of step 1, a salt or carboxylic acid derivative thereof, or a mixture thereof with hydrogen and ammonia.

2. The method according to claim 1, wherein the solvent is an aqueous solvent or an organic solvent having a polarity value of 0 to 0.3.

3. The method according to claim 1, wherein the solvent is an organic solvent containing more than 50 vol % of at least one selected from the group consisting of ether solvents and ester solvents.

4. The method according to claim 1, wherein the solvent is an organic solvent containing more than 50 vol % of at least one selected from tetrahydrofuran, dioxane, 1,2-dimethoxyethane, diglyme, and ethyl acetate.

5. The method according to claim 1, wherein step 1 is carried out under conditions of (i) or (ii):
   (i) in an aqueous solvent at a reaction temperature of 0° C. to 50° C.;
   (ii) in an organic solvent having a polarity value of 0 to 0.3 at a reaction temperature of not lower than 0° C. and lower than 75° C.

6. The method according to claim 1, wherein step 2 is carried out in the presence of a catalyst.

7. The method according to claim 6, wherein the catalyst used in step 2 comprises one or more metals selected from the group consisting of palladium, platinum, ruthenium, rhodium, rhenium, nickel, iridium, osmium, copper and chromium.

8. The method according to claim 1, wherein the catalyst used in step 1 comprises one or more metals selected from the group consisting of palladium, platinum, ruthenium, rhodium, rhenium, nickel, iridium, osmium, copper, and chromium.

9. The method according to claim 8, wherein the metal is supported on at least one support selected from the group consisting of alumina, carbon, silica, titania, zirconia, tantalum oxide, niobium oxide, and zeolite.

10. The method according to claim 1, wherein the partial pressure of hydrogen in step 1 and step 2 is 0.1 MPa to 10 MPa at ordinary temperature in terms of gauge pressure.

11. The method according to claim 1, wherein the reaction temperature in step 2 is 150° C. to 280° C.

12. The method according to claim 2, wherein the solvent is an organic solvent containing more than 50 vol % of at least one selected from the group consisting of ether solvents and ester solvents.

13. The method according to claim 2, wherein the solvent is an organic solvent containing more than 50 vol % of at least one selected from tetrahydrofuran, dioxane, 1,2-dimethoxyethane, diglyme, and ethyl acetate.

14. The method according to claim 2, wherein step 1 is carried out under conditions of (i) or (ii):
   (i) in an aqueous solvent at a reaction temperature of 0° C. to 50° C.;

(ii) in an organic solvent having a polarity value of 0 to 0.3 at a reaction temperature of not lower than 0° C. and lower than 75° C.

15. The method according to claim 2, wherein step 2 is carried out in the presence of a catalyst.

16. The method according to claim 3, wherein the solvent is an organic solvent containing more than 50 vol % of at least one selected from tetrahydrofuran, dioxane, 1,2-dimethoxyethane, diglyme, and ethyl acetate.

17. The method according to claim 3, wherein step 1 is carried out under conditions of (i) or (ii):
 (i) in an aqueous solvent at a reaction temperature of 0° C. to 50° C.;
 (ii) in an organic solvent having a polarity value of 0 to 0.3 at a reaction temperature of not lower than 0° C. and lower than 75° C.

18. The method according to claim 3, wherein step 2 is carried out in the presence of a catalyst.

19. The method according to claim 4, wherein step 1 is carried out under conditions of (i) or (ii):
 (i) in an aqueous solvent at a reaction temperature of 0° C. to 50° C.;
 (ii) in an organic solvent having a polarity value of 0 to 0.3 at a reaction temperature of not lower than 0° C. and lower than 75° C.

20. The method according to claim 4, wherein step 2 is carried out in the presence of a catalyst.

21. A method of producing 3-hydroxyadipic acid comprising mixing at least one selected from the group consisting of 3-oxoadipic acid and salts thereof with a catalyst in the presence of hydrogen under the conditions of (i) or (ii):
 (i) in an aqueous solvent at a reaction temperature of 0° C. to 50° C.;
 (ii) in an organic solvent having a polarity value of 0 to 0.3 at a reaction temperature of not lower than 0° C. and lower than 75° C.

\* \* \* \* \*

UNITED STATES PATENT AND TRADEMARK OFFICE
CERTIFICATE OF CORRECTION

| | |
|---|---|
| PATENT NO. | : 10,364,218 B2 |
| APPLICATION NO. | : 15/758664 |
| DATED | : July 30, 2019 |
| INVENTOR(S) | : Tsukamoto et al. |

Page 1 of 1

It is certified that error appears in the above-identified patent and that said Letters Patent is hereby corrected as shown below:

In the Specification

At Table 1, Line 8 (Example 3), under the subheading "Catalyst", please change "Pd/ZrO$_2$" to -- Pd/Ta$_2$O$_5$ --.

Signed and Sealed this
Twenty-fourth Day of December, 2019

Andrei Iancu
*Director of the United States Patent and Trademark Office*